(12) United States Patent
Zhang et al.

(10) Patent No.: US 11,253,676 B2
(45) Date of Patent: Feb. 22, 2022

(54) INTERVENTIONAL MEDICAL DEVICE DELIVERY SYSTEM

(71) Applicant: HANGZHOU NUO MAO MEDICAL TECHNOLOGY CO., LTD, Zhejiang (CN)

(72) Inventors: Tingchao Zhang, Zhejiang (CN); Yang Li, Zhejiang (CN)

(73) Assignee: HANGZHOU NUO MAO MEDICAL TECHNOLOGY CO., LTD, Hangzhou (CN)

(*) Notice: Subject to any disclaimer, the term of this patent is extended or adjusted under 35 U.S.C. 154(b) by 256 days.

(21) Appl. No.: 16/474,249

(22) PCT Filed: Mar. 10, 2017

(86) PCT No.: PCT/CN2017/076354
§ 371 (c)(1),
(2) Date: Jun. 27, 2019

(87) PCT Pub. No.: WO2018/161359
PCT Pub. Date: Sep. 13, 2018

(65) Prior Publication Data
US 2020/0121891 A1    Apr. 23, 2020

(51) Int. Cl.
*A61M 25/00* (2006.01)
*A61B 17/00* (2006.01)
(Continued)

(52) U.S. Cl.
CPC ... *A61M 25/0097* (2013.01); *A61B 17/00234* (2013.01); *A61M 39/06* (2013.01);
(Continued)

(58) Field of Classification Search
CPC .............. A61M 25/0097; A61M 39/06; A61M 39/1011; A61B 17/00234;
(Continued)

(56) References Cited

U.S. PATENT DOCUMENTS

| 6,270,520 | B1 | 8/2001 | Inoue | |
| 2001/0020184 | A1* | 9/2001 | Dehdashtian | A61F 2/07 623/1.16 |
| 2009/0240326 | A1* | 9/2009 | Wilson | A61F 2/2427 623/2.11 |

FOREIGN PATENT DOCUMENTS

| CN | 104373903 A | 2/2015 |
| CN | 104905890 A | 9/2015 |

(Continued)

OTHER PUBLICATIONS

International Search Report of PCT Patent Application No. PCT/CN2017/076354 dated May 3, 2017.
(Continued)

*Primary Examiner* — Richard G Louis

(57) ABSTRACT

An interventional medical device delivery system comprises a loader provided with a loading tube, a delivery sheath, a dilator, a pushing component, and a hemostasis valve. The loading tube or the delivery sheath is provided with a position-limiting locking connector. An appropriate-rotation control mechanism for controlling a tightening degree between a distal end of the loading tube and a proximal end of the delivery sheath is disposed outside the loading tube or the delivery sheath. The proximal end of the delivery sheath and the distal end of the loading tube engage with each other in a sealed manner, and are threadingly fixed to each other by means of the position-limiting locking connector. The appropriate-rotation control mechanism rotates in one direction to appropriately tighten a thread-connection, and rotates in the opposite direction to release the thread-connection. The interventional medical device conveying system of the invention automatically determines a tightening degree.

10 Claims, 8 Drawing Sheets

(51) Int. Cl.
| | |
|---|---|
| *A61M 39/06* | (2006.01) |
| *A61B 17/12* | (2006.01) |
| *A61M 39/10* | (2006.01) |
| *A61F 2/01* | (2006.01) |

(52) U.S. Cl.
CPC .......... *A61B 17/12109* (2013.01); *A61B 2017/00292* (2013.01); *A61B 2017/1205* (2013.01); *A61F 2/011* (2020.05); *A61M 39/1011* (2013.01)

(58) Field of Classification Search
CPC .... A61B 17/12109; A61B 2017/00292; A61B 2017/1205; A61B 2017/0053; A61B 17/12172; A61B 2017/00407; A61B 2017/00477; A61B 2017/00575; A61B 2017/00623; A61B 17/12022; A61F 2/011; A61F 2/9522; A61F 2220/0041; A61F 2/966
See application file for complete search history.

(56) References Cited

FOREIGN PATENT DOCUMENTS

| GB | 2509952 A | 7/2014 |
|---|---|---|
| WO | 99/56668 A1 | 11/1999 |

OTHER PUBLICATIONS

Extended European Search Report of counterpart European Patent Application No. 17900128.4 dated Nov. 14, 2019.

\* cited by examiner

INTERVENTIONAL MEDICAL DEVICE DELIVERY SYSTEM

TECHNICAL FIELD

The present invention belongs to the technical field of medical device, and relates to an interventional medical device delivery system.

BACKGROUND

The minimally invasive interventional procedure is becoming more and more widely used in clinical applications. A delivery system for an intracavity interventional instrument (such as an occluder, a vascular plug, a filter, etc.) generally at least includes several parts such as a delivery sheath, a dilator, a loader, a hemostasis valve, and a pushing component (e.g., a steel cable). A channel is established using the delivery sheath and the dilator, then the dilator is withdrawn from the channel, and the interventional device is received into the loader through the pushing component and then introduced into the delivery sheath to further transport the interventional instrument to a targeted location. During the process of introducing the interventional device from the loader into the delivery sheath, the connection and fitting between the loader and the delivery sheath is very essential. This position for connection and fitting requires that a distal end of a loading tube of the loader is seamlessly connected to an end surface of a proximal end of the delivery sheath, and the inner cavities of the loading tube and the delivery sheath transit smoothly, so as to ensure the smooth passage of the device. For an endovascular interventional device, this position also requires maintaining a seal to ensure that the risk of air embolism is reduced during the exhausting process of the device.

The loader and the delivery sheath are usually connected threadingly. The distal end of the loading tube of the loader is threadingly connected to an joint of the delivery sheath, where by continuous tightening together of threads, the distal end of the loading tube abuts against the proximal end of the delivery sheath, and if the tightening degree is not enough, the connection between the distal end of the loading tube and the proximal end of the delivery sheath is not in place, there is a gap at the connection position, such that the interventional device tends to be jammed during pushing, especially for a structure having a barb or a monofilament end, and at this time if the interventional device is pushed forcibly, it may cause deformation or broken of the device in serious cases, which in turn causes the failure of an operation. Additionally, if there is a gap at the connection position, the seal of the loader and the delivery sheath cannot be kept, and thus during the exhausting process of the device through the hemostasis valve, the delivery system tends to cause air embolism due to poor exhausting.

In clinical practice, in order to achieve a seamless connection between the distal end of the loader and the proximal end of the delivery sheath and a smooth transition of the inner cavities of them, so as to ensure the seal at connection position between the distal end of the loader and the proximal end of the delivery sheath to reduce the risk of air embolism, the doctor often tends to excessively rotate the thread. However, if the tightening degree is excessive, the distal end of the loading tube of the loader is easily deformed by extrusion, and thus results in a neck-in effect, such that the inner diameter at the distal end of the loading tube is reduced and results in difficulty for the device to pass through, and at this time if the interventional device is pushed forcibly, it may cause deformation or broken of the device in serious cases, which in turn causes the failure of an operation. If the degree of rotation is not enough, the connection between the distal end of the loading tube and the proximal end of the delivery sheath is not in place, and there is a gap at the connection position, such that the interventional device tends to be jammed during pushing, and meanwhile air embolism is caused due to the poor exhausting; and the aforementioned structure cannot determine if the device has been assembled in place, and it requires the doctor to operate by experience.

TECHNICAL PROBLEM

The loader and the delivery sheath are usually connected threadingly. The distal end of the loading tube of the loader is threadingly connected to an joint of the delivery sheath, where by continuous tightening together of threads, the distal end of the loading tube abuts against the proximal end of the delivery sheath, and if the tightening degree is not enough, the connection between the distal end of the loading tube and the proximal end of the delivery sheath is not in place, there is a gap at the connection position, such that the interventional device tends to be jammed during pushing, especially for a structure having a barb or a monofilament end, and at this time if the interventional device is pushed forcibly, it may cause deformation or broken of the device in serious cases, which in turn causes the failure of an operation. Additionally, if there is a gap at the connection position, the seal of the loader and the delivery sheath cannot be kept, and thus during the exhausting process of the device through the hemostasis valve, the delivery system tends to cause air embolism due to poor exhausting.

In clinical practice, in order to achieve a seamless connection between the distal end of the loader and the proximal end of the delivery sheath and a smooth transition of the inner cavities of them, so as to ensure the seal at connection position between the distal end of the loader and the proximal end of the delivery sheath to reduce the risk of air embolism, the doctor often tends to excessively rotate the thread. However, if the tightening degree is excessive, the distal end of the loading tube of the loader is easily deformed by extrusion, and thus results in a neck-in effect, such that the inner diameter at the distal end of the loading tube is reduced and results in difficulty for the device to pass through, and at this time if the interventional device is pushed forcibly, it may cause deformation or broken of the device in serious cases, which in turn causes the failure of an operation. If the degree of rotation is not enough, the connection between the distal end of the loading tube and the proximal end of the delivery sheath is not in place, and there is a gap at the connection position, such that the interventional device tends to be jammed during pushing, and meanwhile air embolism is caused due to the poor exhausting; and the aforementioned structure cannot determine if the device has been assembled in place, and it requires the doctor to operate by experience.

SUMMARY

The technical problem to be solved by the present invention is to provide an interventional medical device delivery system which has a simple structure, is easy to operate, and automatically determines a tightening degree, in view of the defects of the prior art.

The technical solution adopted by the present invention to solve the technical problem thereof is as follows.

An interventional medical device delivery system includes a loader provided with a loading tube, a delivery sheath, a dilator, a pushing component and a hemostasis valve; where the loading tube or the delivery sheath is provided with a position-limiting locking connector thereon;

an appropriate-rotation control mechanism for controlling a tightening degree between a distal end of the loading tube and a proximal end of the delivery sheath is disposed outside the loading tube or the delivery sheath;

the proximal end of the delivery sheath and the distal end of the loading tube engage with each other in a sealed manner, and are threadingly fixed to each other by means of the position-limiting locking connector; and the appropriate-rotation control mechanism rotates in one direction to appropriately tighten a thread-connection, and rotates in the opposite direction to release the thread-connection.

In the interventional medical device delivery system, preferably the position-limiting locking connector and the appropriate-rotation control mechanism are simultaneously sleeved outside the loading tube or the delivery sheath; the appropriate-rotation control mechanism and the position-limiting locking connector are engaged, fixedly connected, or detachably fixed with each other; the position-limiting locking connector is provided with an internal thread, the delivery sheath or loading tube is provided with an external thread correspondingly, and the internal thread and the external thread are threadingly connected to connect the loading tube and the delivery sheath together.

In the interventional medical device delivery system, preferably the appropriate-rotation control mechanism is detachably fixed with the position-limiting locking connector through an elastic positioning member and a snapping position; the position-limiting locking connector is provided with the elastic positioning member on the outer wall thereof, the appropriate-rotation control mechanism is provided with the snapping position thereon correspondingly, the elastic positioning member is elastically snapped into the snapping position to detachably fix the appropriate-rotation control mechanism and the position-limiting locking connector, and under an external force, the elastic positioning member elastically contracts and thus is detached from the snapping position to release the fixation between the appropriate-rotation control mechanism and the position-limiting locking connector; or alternatively, the appropriate-rotation control mechanism is provided with the elastic positioning member, and the position-limiting locking connector is provided with a snapping position thereon correspondingly, the elastic positioning member is elastically snapped into the snapping position to detachably fix the appropriate-rotation control mechanism and the position-limiting locking connector, and under an external force, the elastic positioning member elastically contracts and thus is detached from the snapping position to release the fixation between the appropriate-rotation control mechanism and the position-limiting locking connector.

In the interventional medical device delivery system, preferably the elastic positioning member is an elastic member which is fixed on the position-limiting locking connector and gradually stretches outwardly from the wall of the position-limiting locking connector, and after the elastic positioning member is elastically snapped into the snapping position, the appropriate-rotation control mechanism is position-limiting fixed and only rotates relative to the position-limiting locking connector; or alternatively, the elastic positioning member is an elastic member which is fixed in the appropriate-rotation control mechanism and gradually stretches from the appropriate-rotation control mechanism to a center, and after the elastic positioning member is snapped into the snapping position, the appropriate-rotation control mechanism is position-limiting fixed and only rotates relative to the position-limiting locking connector.

In the interventional medical device delivery system, preferably the appropriate-rotation control mechanism and the position-limiting locking connector are respectively disposed outside the loading tube or the delivery sheath, and after the loading tube or the delivery sheath is engaged, the appropriate-rotation control mechanism and the position-limiting locking connector are engaged with each other, such that the appropriate-rotation control mechanism drives the position-limiting locking connector to rotate.

In the interventional medical device delivery system, preferably the position-limiting locking connector and the appropriate-rotation control mechanism are connected through a connecting sleeve; and the position-limiting locking connector and the connecting sleeve, as well as the connecting sleeve and the appropriate-rotation control mechanism, are each detachably connected.

In the interventional medical device delivery system, preferably the position-limiting locking connector, the connecting sleeve and the appropriate-rotation control mechanism are each provided with an elastic positioning member and/or a snapping position thereon; and the position-limiting locking connector and the connecting sleeve, as well as the connecting sleeve and the appropriate-rotation control mechanism, are detachably fixed together through the elastic positioning member being elastically snapped into the snapping position.

In the interventional medical device delivery system, preferably the appropriate-rotation control mechanism includes a handwheel, the handwheel is therein provided with a driving connector that is detachably fixed to the connecting sleeve or the position-limiting locking connector, and an appropriate-stopper is arranged between the handwheel and the driving connector; the handwheel drives the driving connector to rotate with a driving force that is less than a force which forces the appropriate-stopper to be deformed to slide out, and the handwheel drives the driving connector to rotate towards a direction by means of the appropriate-stopper; when the driving force by which the handwheel drives the driving connector to rotate during tightening causes that the appropriate-stopper is deformed to slide out, the handwheel independently rotates relative to the driving connector.

In the interventional medical device delivery system, preferably the appropriate-stopper is at least one elastic snap head disposed on an inner wall of the handwheel, and the corresponding driving connector is provided with multiple snap grooves on an outer wall thereof; or alternatively the appropriate-stopper is at least one elastic snap head disposed on an outer wall of the driving connector, and the handwheel is correspondingly provided with multiple snap grooves on an inner wall thereof;

each snap groove is provided with a first sliding surface on a side wall thereof; after the elastic snap head is snapped into the snap groove, an end portion of the elastic snap head is lap-jointed with the first sliding surface, and the rotation of the handwheel drives the driving connector to rotate; and when the driving connector is stopped as subjected to a rotation resistance, the rotation of the handwheel forces the elastic snap head to deform elastically and thus slides out from the snap groove through the first sliding surface, and the handwheel spins relative to the driving connector; a side surface of the snap groove that is opposite to the first sliding surface is a first stopping surface, and an end portion of the elastic snap head is lap-jointed with the first stopping surface such that the handwheel rotates in an opposite direction to drive the driving connector to rotate.

In the interventional medical device delivery system, preferably the driving connector has a connection end that extends outwardly along an axial direction, the connection end is opened in an axial direction and is provided with an internal thread on an inner wall thereof, and the internal thread of the connection end is threadingly connected to an external thread at a proximal end of the delivery sheath or an external thread at a distal end of the loading tube so as to fixedly connect the proximal end of the delivery sheath and the distal end of the loading tube together; or alternatively the appropriate-rotation control mechanism is provided with a connection head therein, the connection head is fixedly connected to or detachably fixed to the appropriate-rotation control mechanism, the connection head is opened at one end thereof in the axial direction and is provided with an internal thread on an inner wall thereof, and the internal thread of the connection head is threadingly connected to an external thread at an proximal end of the delivery sheath or an external thread at a distal end of the loading tube to fixedly connect the proximal end of the delivery sheath and the distal end of the loading tube together.

In the interventional medical device delivery system, preferably the elastic snap head is a helical spring strip, or an elastic pawl that is bendable under a force; or alternatively the elastic snap head includes an elastic member, and a top-pressing member disposed at a front end of the elastic member.

The present invention adopts a manner of disposing the position-limiting locking connector and the appropriate-rotation control mechanism on the loading tube of the loader and the delivery sheath to control the tightening degree. When it is tightened to an appropriate position, an end surface at the distal end of the loading tube presses the proximal end of the delivery sheath and thus is subjected to a resistance from the delivery sheath, and the resistance will be transmitted to the appropriate-rotation control mechanism, such that when the appropriate-rotation control mechanism is rotated continually, the appropriate-rotation control mechanism cannot rotate continually due to the subjected resistance. As such, under the simultaneous action of the driving force and the resistance, the structure of the appropriate-rotation control mechanism is elastically deformed under a force, and when the deformation is accumulated to a certain extent, a slipping phenomenon occurs, and thus the threads of the loader and the delivery sheath cannot be tightened together continually any more, thereby avoiding the problem that the device cannot be transported since the end surface at the distal end of the loading tube is deformed by extrusion and the inner cavity is reduced due to the too tight assembly. At the same time, the slipping phenomenon can also prompt the doctor that the delivery sheath and the loading tube device have been assembled in place, that is, a seamless connection between the loader and the end face of the delivery sheath is achieved, the connection of their inner cavities is smooth, and meanwhile the radial bevels are abutted to seal between the distal end of the loading tube and the proximal end of the delivery sheath. If no slipping phenomenon occurs, it indicates that the delivery sheath and the loading tube have not been assembled in place yet, and it is still necessary to continue to tighten until the slipping phenomenon occurs.

Therefore, the present invention has a simple structure, is easy to operate, and automatically determines that the delivery sheath and the loading tube have been assembled in place.

BRIEF DESCRIPTION OF THE DRAWINGS

The present invention will be further illustrated in connection with accompanying drawings and embodiments, in which.

DETAILED DESCRIPTION

For a better understanding of the technical features, the objects and the effects of the present invention, the specific embodiments of the present invention will be described in detail with reference to the accompanying drawings.

Definition of orientation: a direction near an operator is a proximal end, and a direction away from the operator is a distal end.

Since the present invention has various technical solutions, the technical solutions will be separately explained by the following several embodiments.

Figure 1:
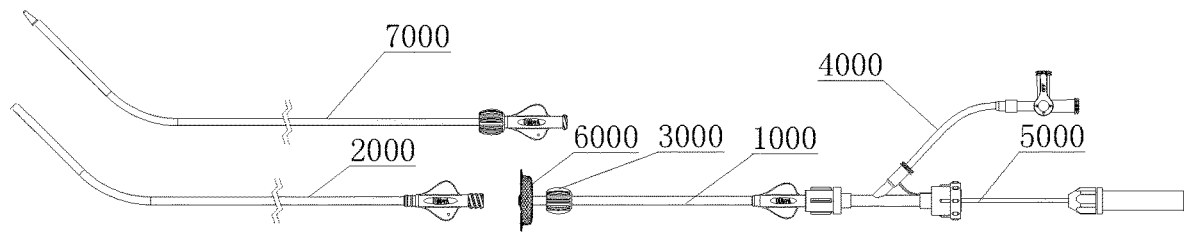
FIG. 1 is a schematic view showing the appearance structure of the present invention.
Figure 2:
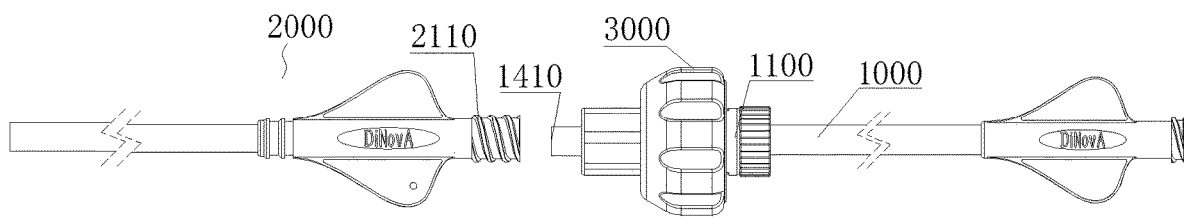
FIG. 2 is a schematic view showing the appearance structure of the detachable fixation between the position-limiting locking connector and the appropriate-rotation control mechanism in Embodiment 1 of the present invention.

As shown in FIGS. 1 and 2, an interventional medical device delivery system includes a loader provided with a loading tube 1000, a delivery sheath 2000, a dilator 7000, a pushing component 5000, and a hemostasis valve 4000. A channel is established through the delivery sheath 2000 and the dilator 7000, then the dilator 7000 is withdrawn from the channel, the pushing component 5000 passes through the loading tube 1000 of the loader and the hemostasis valve 4000, then the interventional device 6000 is received into the loading tube 1000 of the loader. A position-limiting locking connector 1100 is disposed on the loading tube 1000 of the loader or the delivery sheath 2000; and an appropriate-rotation control mechanism 3000 for controlling the tightening degree of the loading tube 1000 and the delivery sheath 2000 is disposed on the loading tube 1000 or the delivery sheath 2000.

Depending on the different disposing positions of the position-limiting locking connector 1100 and the appropriate-rotation control mechanism 3000, there are many forms of connection relationships therebetween. The first one is that the position-limiting locking connector 1100 and the appropriate-rotation control mechanism 3000 are simultaneously sleeved outside the loading tube 1000, or simultaneously sleeved outside the delivery sheath 2000; the appropriate-rotation control mechanism 3000 and the position-limiting locking connector 1100 are engaged, fixedly connected, or detachably fixed with each other. Another one is that the appropriate-rotation control mechanism 3000 and the position-limiting locking connector 1100 are respectively disposed outside the loading tube or the delivery sheath; the appropriate-rotation control mechanism 3000 and the position-limiting locking connector 1100 are separated from each other when they are not assembled, and the appropriate-rotation control mechanism 3000 and the position-limiting locking connector 1100 are engaged with each other only when the loading tube or the delivery sheath is engaged, such that the appropriate-rotation control mechanism 3000 can drive the position-limiting locking connector 1100 to rotate. The following is explained in detail with different Embodiments.

Embodiment 1, as shown in FIGS. 2-18, in the interventional medical device delivery system, the position-limiting locking connector 1100 and the appropriate-rotation control mechanism 3000 are disposed on the loading tube 1000 of the loader; the appropriate-rotation control mechanism 3000 and the position-limiting locking connector 1100 are engaged, fixedly connected, or detachably fixed with each other. The position-limiting locking connector 1100, the loading tube 1000 and the appropriate-rotation control mechanism 3000 are installed coaxially. The loading tube 1000 and the delivery sheath 2000 engage with each other in a sealed manner, and are threadingly fixed to each other by means of the position-limiting locking connector 1100; and the appropriate-rotation control mechanism 3000 rotates in one direction to appropriately tighten a thread-connection, and rotates in the opposite direction to release the thread-connection.

As shown in FIG. 2, the delivery sheath 2000 is provided with an external thread 2110 on an outer wall at the end port thereof, and is provided with a frustum-shaped surface on an inner wall at the end port thereof and the frustum-shaped surface has a diameter that is gradually reduced inwardly from the end port, the minimum diameter of the frustum-shaped surface is consistent with an outer diameter of the loading tube 1000, and an annular stage 2111 is disposed at the portion with the minimum diameter, the inner diameter at the stage 2111 is the same as that of the loading tube 1000, such that the end surface 1410 of the loading tube 1000 abuts against the stage 2111, the inner walls of the loading tube 1000 and the delivery sheath 2000 transit smoothly to ensure the smooth passage of an device, meanwhile the end surface of the loading tube 1000 abuts against the stage 2111 to achieve seamless connection, thereby maintaining the seal, ensuring the avoidance of gas leakage during the exhausting process of the device, and thus lowering the risk of air embolism, and finally the device is smoothly introduced from the loading tube 1000 into the delivery sheath 2000.

Figure 3:
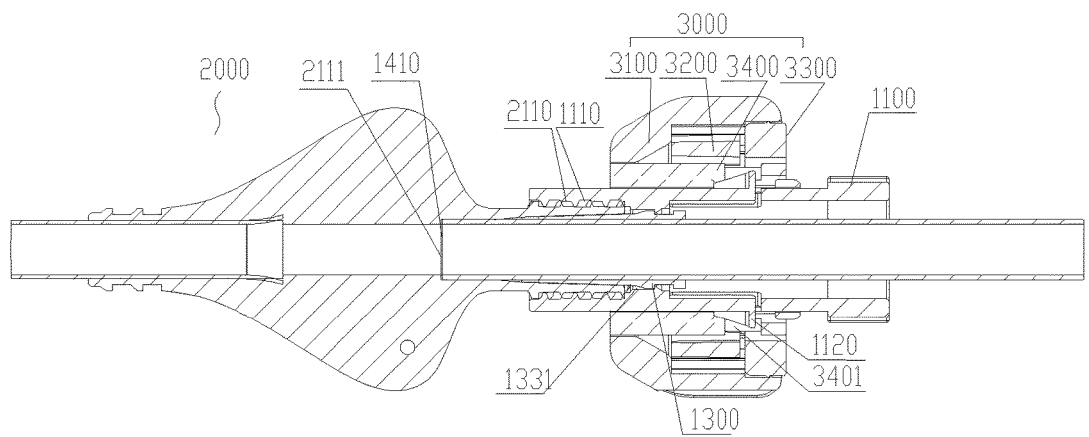
FIG. 3 is a cross-sectional view showing the detachable fixation between the position-limiting locking connector and the appropriate-rotation control mechanism in Embodiment 1 of the present invention.

As shown in FIGS. 2 and 3, the position-limiting locking connector 1100 is a tubular structure with two ends thereof being penetrated, and the position-limiting locking connector 1100 is sleeved on the loading tube 1000 by a detachable position-limiting fixation manner or in a direct position-limiting fixation manner, and the detachable position-limiting fixation manner adopts snap connection. By limiting the axial movement of the position-limiting locking connector 1100 via a snap position disposed on the outer wall of the loading tube 1000, the position-limiting locking connector 1100 can only rotate, and cannot move axially. Particularly, the position-limiting locking connector 1100 is provided with an annular snap groove 1300 on the inner wall thereof, and the loading tube 1000 is provided with a snap head 1331 on the outer wall thereof correspondingly. The position-limiting locking connector 1100 is sleeved onto the loading tube 1000, and the snap head 1331 is snapped into the corresponding snap groove 1300 to connect the position-limiting locking connector 1100 and the loading tube 1000 together in a position-limiting manner, such that the position-limiting locking connector 1100 can axially rotate about the loading tube 1000, but cannot move back and forth axially. The positions of the snap head 1331 and the snap groove 1300 can also be exchanged, such that the snap groove is arranged on the loading tube 1000, and the snap head is arranged on the inner wall of the position-limiting locking connector 1100.

Figure 5:
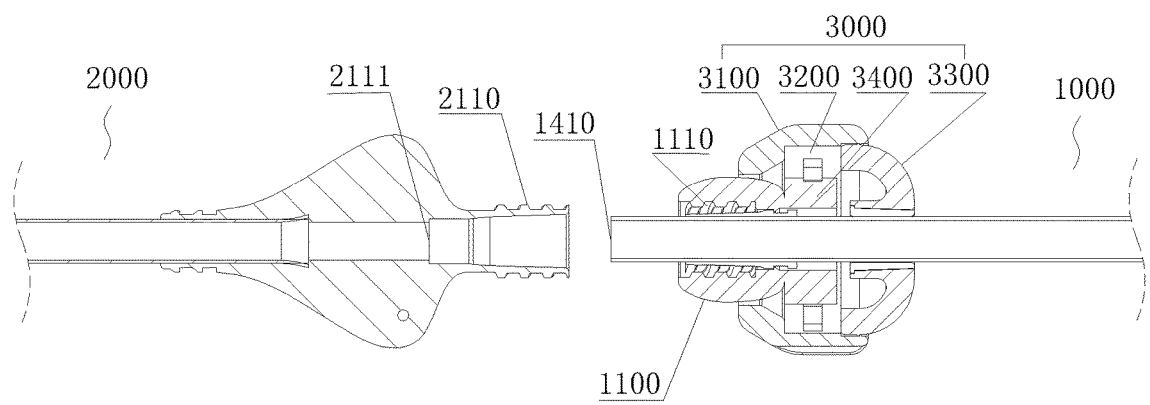
FIG. 5 is a cross-sectional view showing the fixed connection between the position-limiting locking connector and the appropriate-rotation control mechanism in Embodiment 1 of the present invention.
Figure 6:
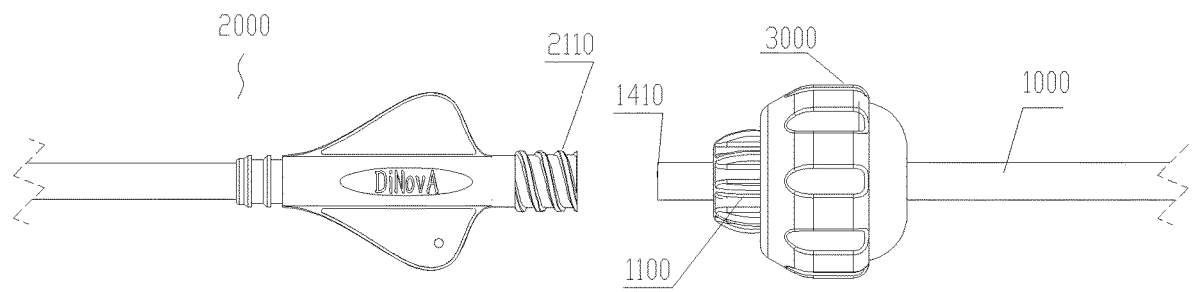
FIG. 6 is a schematic view showing the appearance structure of the engagement between the position-limiting locking connector and the appropriate-rotation control mechanism in Embodiment 1 of the present invention.

As shown in FIGS. 3, 5 and 6, the position-limiting locking connector 1100 is provided with an internal thread 1110 since it is to be connected with the delivery sheath 2000, and the delivery sheath 2000 is provided with an external thread 2110 correspondingly. The two threads are threadingly connected to connect the delivery sheath 2000 and the loading tube 1000 together fixedly.

As shown in FIGS. 2 and 3, the appropriate-rotation control mechanism 3000 and the position-limiting locking connector 1100 are detachably fixed with each other; and as shown in FIG. 5, the appropriate-rotation control mechanism 3000 and the position-limiting locking connector 1100 are fixedly connected with each other.

There are many manners for achieving the detachable fixation between the position-limiting locking connector 1100 and the appropriate-rotation control mechanism 3000, such as a snap connection, a thread connection, a pin connection, and the like, and the snap connection manner is adopted in this Embodiment. The appropriate-rotation control mechanism 3000 and the position-limiting locking connector 1100 are detachably fixed with each other through the elastic positioning member and the snapping position.

Figure 4:
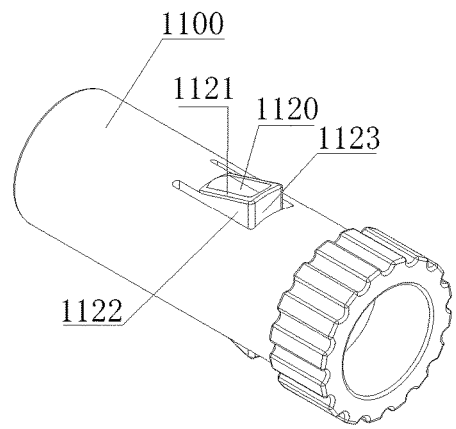
FIG. 4 is a schematic structural view of the position-limiting locking connector in Embodiment 1 of the present invention.

As shown in FIGS. 3 and 4, a first implementation of snap connection is that: the position-limiting locking connector 1100 is provided with an elastic positioning member 1120 on an outer wall thereof, and the appropriate-rotation control mechanism 3000 is provided with a snapping position 3401 therein correspondingly. Particularly, the snapping position 3401 is disposed on the surface of the inner wall of the driving connector 3400, and the snapping position 3401 is a snap groove or a snap hole. The elastic positioning member is elastically snapped into the snapping position 3401 to fix the appropriate-rotation control mechanism 3000 and the position-limiting locking connector 1100 together detachably.

The elastic positioning member 1120 is an elastic member which gradually stretches from the surface of the position-limiting locking connector 1100 outwardly. The elastic positioning member 1120 may be of many structures, such as a snap bead, a spring strip, and the like, and preferably is the spring strip set in an angled shape as shown in FIG. 3. As shown in FIGS. 2 and 3, the elastic positioning member 1120 includes a bevel 1121 which stretches from the surface of the position-limiting locking connector 1100 outwardly. When the appropriate-rotation control mechanism 3000 slides along the bevel 1121 on the elastic positioning member 1120 of the position-limiting locking connector 1100, the elastic positioning member 1120 is extruded by the surface of the inner wall of the driving connector 3400 and thus moves into the position-limiting locking connector 1100, such that the appropriate-rotation control mechanism 3000 is sleeved onto the position-limiting locking connector 1100, and when the appropriate-rotation control mechanism 3000 slides to the snapping position 3401 of the appropriate-rotation control mechanism 3000, the extruded elastic positioning member 1120 is ejected towards the snapping position 3401 and thus snapped into the snapping position 3401, such that the position-limiting locking connector 1100 and the appropriate-rotation control mechanism 3000 are assembled together. The lateral end surfaces 1122 on two sides of the bevel 1121 of the elastic positioning member 1120 limits the spinning of the appropriate-rotation control mechanism 3000, and the end surface 1123 located at the proximal end of the bevel 1121 limits the appropriate-rotation control mechanism 3000 in such a manner that the appropriate-rotation control mechanism 3000 can only continually move forward rather than move backward relative to the position-limiting locking connector 1100. As such, the appropriate-rotation control mechanism 3000 is on the position-limiting locking connector 1100.

A second implementation of snap connection is that: an elastic positioning member is disposed on the inner wall of the appropriate-rotation control mechanism 3000, i.e., on the surface of the inner wall of the driving connector 3400, and a snapping position is disposed on the corresponding surface of the position-limiting locking connector 1100. The elastic positioning member is elastically snapped into the snapping position, such that the appropriate-rotation control mechanism 3000 and the position-limiting locking connector 1100 are fixed detachably. The elastic positioning member is an elastic member which gradually stretches from the surface of the inner wall of the appropriate-rotation control mechanism 3000 to the center thereof, and the elastic positioning member is snapped into the snapping position to limit the appropriate-rotation control mechanism 3000 in such a manner that the appropriate-rotation control mechanism 3000 can only rotate and move backward relative to the position-limiting locking connector 1100. The specific structure is the same as that of the first snapping implementation, and thus will not be repeated anymore here.

As shown in FIG. 5, the driving connector 3400 and the position-limiting locking connector 1100 are fixedly connected coaxially, or they are integrated as a one-piece structure. The appropriate-rotation control mechanism 3000 and the position-limiting locking connector 1100 are fixedly connected. That is, the position-limiting locking connector 1100 and the appropriate-rotation control mechanism 3000 are fixed as a whole. That is, the position-limiting locking connector 1100 becomes a part of the axial extension of the appropriate-rotation control mechanism 3000. The position-limiting locking connector 1100 is provided with an internal thread 1110 therein.

As shown in FIGS. 5-8, the position-limiting locking connector 1100 and the appropriate-rotation control mechanism 3000, which are simultaneously disposed outside the loading tube 1000, engage with each other. There are many engagement manners, and generally the engagement manner is that an engagement block and an engagement groove, which are disposed axially, engage with each other. As shown in FIGS. 5a-6, the position-limiting locking connector 1100 is provided with a connection head 1101 at an end portion thereof, an engagement groove 1102 is disposed axially on the connection head 1101 as shown, and an engagement block is disposed axially on the appropriate-rotation control mechanism 3000 correspondingly, such that after the engagement block is engaged into the engagement groove 1102, the appropriate-rotation control mechanism 3000 drives the position-limiting locking connector 1100 to rotate about the axial direction. Alternatively, an engagement block is disposed axially on the outer wall of the position-limiting locking connector 1100, and an engagement groove is disposed axially on the appropriate-rotation control mechanism 3000 correspondingly, the engagement block and the engagement groove engage with each other.

In addition to being disposed on the loading tube 1000 of the loader, the position-limiting locking connector 1100 and the appropriate-rotation control mechanism 3000 may also simultaneously disposed on the delivery sheath 2000. The connection relationship between the position-limiting locking connector 1100 and the appropriate-rotation control mechanism 3000 is the same as above, and thus will not be repeated anymore here.

Figure 7:
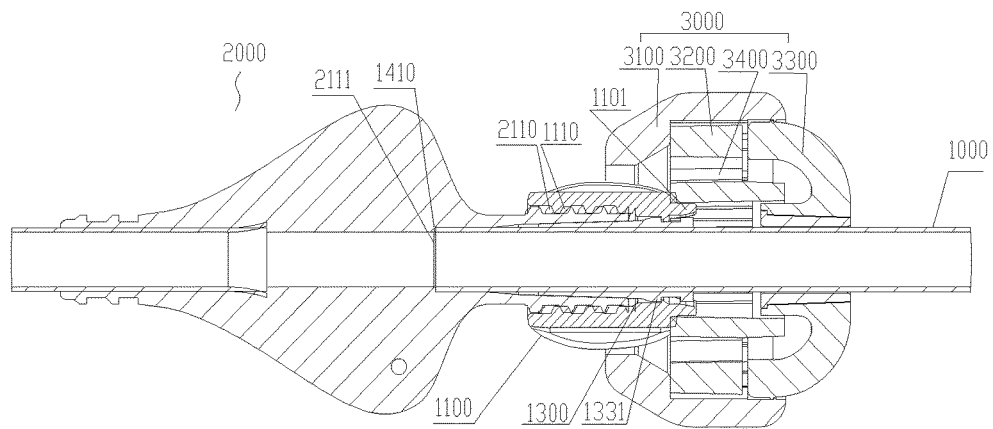
FIG. 7 is a cross-sectional view showing the engagement between the position-limiting locking connector and the appropriate-rotation control mechanism in Embodiment 1 of the present invention.
Figure 8:
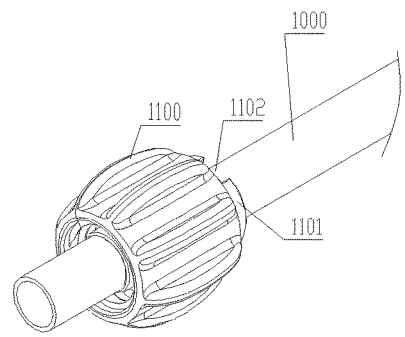
FIG. 8 is a schematic view showing the appearance structure of the position-limiting locking connector in Embodiment 1 of the present invention.

As shown in FIGS. 3, 5 and 7, the appropriate-rotation control mechanism 3000 includes a handwheel 3100, the handwheel 3100 is therein provided with a driving connector 3400 that is detachably fixed to the position-limiting locking connector 1100, and an appropriate-stopper 3200 is arranged between the handwheel 3100 and the driving connector 3400; the handwheel 3100 drives the driving connector 3400 to rotate with a driving force that is less than a force which forces the appropriate-stopper to be deformed and slide out, and the handwheel 3100 drives the driving connector 3400 to rotate towards a direction by means of the appropriate-stopper; once the driving force by which the handwheel 3100 drives the driving connector 3400 to rotate during tightening causes that the appropriate-stopper is deformed and slides out, the handwheel 3100 independently rotates relative to the driving connector 3400.

In addition to the main structure consisting of the handwheel 3100, the driving connector 3400 and the appropriate-stopper 3200, the appropriate-rotation control mechanism 3000 also includes a retaining ring 3300 disposed on an end portion of the handwheel 3100. The retaining ring 3300 seals the handwheel 3100, and the driving connector 3400 and the appropriate-stopper 3200 are located in a space sealed by the retaining ring 3300 and the handwheel 3100. The appropriate-stopper 3200 is located on the surface of the outer wall of the driving connector 3400, or may be located on the inner wall of the handwheel 3100. When the appropriate-stopper 3200 is located on the surface of the outer wall of the driving connector 3400, the driving connector 3400 and the appropriate-stopper 3200 can be integrally made, or may be connected together fixedly. Also, when the appropriate-stopper 3200 is located on the inner wall of the handwheel 3100, the appropriate-stopper 3200 and the handwheel 3100 can be integrally made, or may be connected together fixedly.

As shown in FIGS. 9-18, the appropriate-stopper 3200 is at least one elastic snap head disposed on the inner wall of the handwheel 3100, and multiple snap grooves 3130 are disposed on the outer wall of the driving connector 3400; or alternatively the appropriate-stopper 3200 is at least one elastic snap head disposed on the outer wall of the driving connector 3400, multiple snap grooves 3130 are disposed on the inner wall of the handwheel 3100, and each snap groove 3130 is provided with a first sliding surface 3110 on the side wall thereof; when the end portion of the elastic snap head is lap jointed with the first sliding surface 3110 after the elastic snap head is snapped into the snap groove 3130, the rotation of the handwheel 3100 drives the driving connector 3400 to rotate; when the driving connector 3400 is stopped as subjected to a rotation resistance, the rotation of the handwheel 3100 forces the elastic snap head to deform elastically and thus slides out from the snap groove 3130 through the first sliding surface 3110, and the handwheel 3100 spins relative to the driving connector 3400. The surface on which the end portion of the elastic snap head is lap jointed with the side wall of the snap groove 3130 is the first sliding surface 3110. The elastic snap head is a helical spring strip, or an elastic pawl that is bendable under a force; or alternatively the elastic snap head includes an elastic member, and a top-pressing member disposed at a front end of the elastic member.

The appropriate-rotation control mechanism 3000 are of multiple structures, and each structure is described in detail hereafter.

Figure 9:
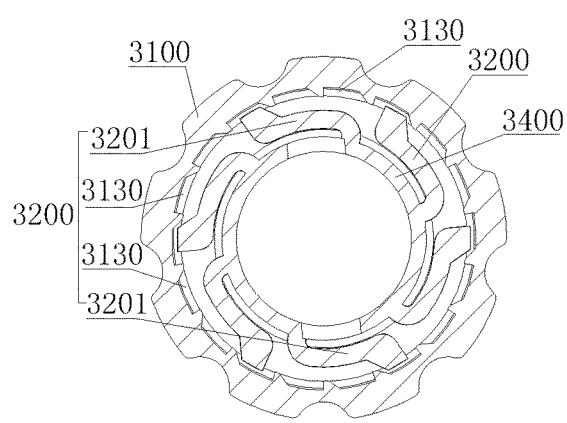
FIG. 9 is a schematic structural view of a first implementation of the appropriate-rotation control mechanism in Embodiment 1 of the present invention.
Figure 10:
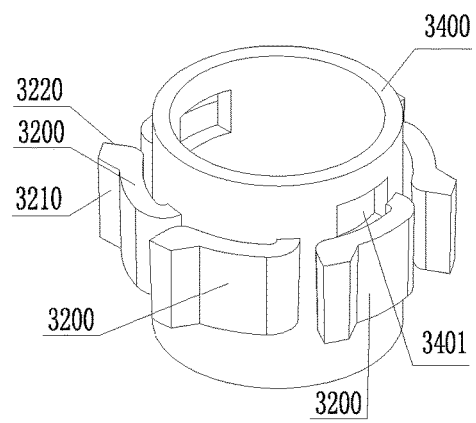
FIG. 10 is a schematic view showing the appearance structure of the driving connector in Embodiment 1 of the present invention.

1. As shown in FIGS. 9 and 10, the first implementation of the appropriate-rotation control mechanism 3000 is as follows.

The appropriate-stopper 3200 is at least one elastic snap head 3201 disposed on the outer wall of the driving connector 3400, and multiple snap grooves 3130 are disposed on the inner wall of the handwheel 3100; the number of the elastic snap heads 3201 is set according to an actual requirement, and may be multiple or one. In this Embodiment, multiple elastic snap heads 3201 are disposed at even intervals along the circumference of the outer wall of the driving connector 3400, and the positions, intervals and number of the snap grooves 3130 disposed on the inner wall of the corresponding handwheel 3100 are consistent with those of the elastic snap heads 3201, or the number of the snap grooves 3130 is greater than those of the elastic snap heads 3201. The elastic snap head 3201 is an elastic pawl which is bendable under a force. The entire shape of the elastic snap head 3201 is not limited and may be a strip shape, a sheet shape, a protruded shape, etc. In order to increase the elastic force of the elastic snap head 3201, mostly a structure, which has a longer length and is disposed in a clockwise or counterclockwise direction, is adopted, to increase the deformation amount of the elastic snap head 3201.

The end portion of the elastic snap head 3201 is snapped with the snap groove 3130, the shape of the elastic snap head 3201 fits for the snapping and is suitable for sliding out, each snap groove 3130 is provided with a first sliding surface 3110 on a side wall thereof, and a first stopping surface 3120 is located on a side surface opposite to the first sliding surface 3110; and the end portions of each elastic snap head 3201 are provided with a second sliding surface 3210 and a second stopping surface 3220 respectively. The surface on which the end portion of the elastic snap head 3201 is lap-jointed with the side wall of the snap groove 3130 is the second sliding surface 3210. When the second sliding surface 3210 at the end portion of the elastic snap head 3201 is lap jointed with the first sliding surface 3110 after the elastic snap head 3201 is snapped into the snap groove 3130, the rotation of the handwheel 3100 drives the driving connector 3400 to rotate, and at this time the threads are tightened normally; and when the loading tube 1000 and the delivery sheath 2000 are assembled in place, they are abutted so as to result in a resistance. When the driving connector 3400 is stopped as subjected to a rotation resistance, the rotation of the handwheel 3100 forces the elastic snap head 3201 to deform elastically and slides out from the snap groove 3130 through the first sliding surface 3110, and the handwheel 3100 spins relative to the driving connector 3400. Both the first sliding surface 3110 and the second sliding surface 3210 are bevels, which are beneficial for sliding of them relative to each other under an appropriate outer force, and the slopes of them may be the same or different. In order to achieve that the elastic snap head 3201 not only can be lap-jointed with the first sliding surface 3110 of the snap groove 3130 to drive the rotation of the appropriate-rotation control mechanism 3000, but also can be detached from the first sliding surface 3110 under the certain external force, the elastic snap head 3201 is preferably lap-jointed with the snap groove 3130 partially. That is, the second sliding surface 3210 contacts the first sliding surface 3110 partially. When the acting force between the snap groove 3130 and the elastic snap head 3201 causes that, when the elastic snap head 3201 is elastically deformed to an extent which exceeds the depth at which the first sliding surface 3110 of the snap groove 3130 engages with the end portion of the elastic snap head 3201, the second sliding surface 3210 of the elastic snap head 3201 slides along the first sliding surface 3110 of the snap groove 3130, the snap groove 3130 is staggered from the elastic snap head 3201, and a slipping phenomenon occurs between the driving connector 3400 and the handwheel 3100.

The second stopping surface 3220 of the elastic snap head 3201 and the first stopping surface 3120 of the snap groove 3130 are both vertical surfaces which are perpendicular to a central axis of the appropriate-rotation control mechanism 3000. That is, both the second stopping surface 3220 and the first stopping surface 3120 are perpendicular to or substantially perpendicular to the axial direction of the rotation.

The operation process: the handwheel 3100 is rotated to drive the rotation of the appropriate-stopper 3200 and the driving connector 3400; under the action of the elastic positioning member 1120, the force is transmitted to the position-limiting locking connector 1100; the internal thread 1110 on the position-limiting locking connector 1100 rotates in situ relative to the loading tube 1000 under the action of the snapping position 1300; by continuously tightening the internal thread 1110 of the position-limiting locking connector 1100 to the external thread 2110 of the delivery sheath 2000 until the end surface 1410 of the loading tube 1000 contacts the stage 2111 of the delivery sheath 2000, the tightening of the internal thread 1110 and the external thread 2110 is prevented, and the position-limiting locking connector 1100 cannot rotate; at this time, the handwheel 3100 is rotated continually, the rotation resistance is increased, and the appropriate-stopper 3200 comes elastically deformed; when the elastic deformation exceeds the depth at which the snap groove 3130 engages with the elastic snap head 3201, the second sliding surface 3210 slides out from the first sliding surface 3110, such that it achieves that the appropriate-rotation control mechanism 3000 is rotated while the position-limiting locking connector 1100 is not rotated, thereby avoiding the damage to the end surface 1410 of the loading tube 1000 due to extrusion deformation caused by the excessive tightening of the threads. The elastic snap head 3201 is elastically deformed as subjected to a resistance, and at the moment when it slides out from the first sliding surface 3110, the elastically-deformed elastic snap head 3201 is recovered and a sound is made, which can prompt an operator that the assembly has been in place, and it does not need to continue to rotate the appropriate-rotation control mechanism 3000. When the appropriate-rotation control mechanism 3000 is rotated in an opposite direction, the second stopping surface 3220 of the elastic snap head 3201 contacts the first stopping surface 3120 of the snap groove 3130, to drive the rotation of the position-limiting locking connector 1100 in the opposite direction; since the second stopping surface 3220 and the first stopping surface 3120 are parallel or substantially parallel to each other, and are perpendicular to the central axis of the rotation, the driving resistance of them is far greater than the force generated when the bevels of the first sliding surface 3110 and the second sliding surface 3210 contact each other; and since when the threads are loosening, the rotating force of the threads is gradually reduced, the rotation of the handwheel 3100 can easily drive the rotation of the position-limiting locking connector 1100, thereby rotating out the loading tube 1000 to achieve the separation of the loading tube 1000 from the delivery sheath 2000.

Figure 11:
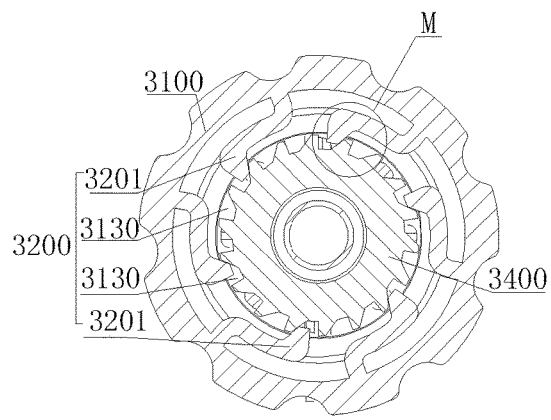
FIG. 11 is a schematic structural view of a second implementation of the appropriate-rotation control mechanism in Embodiment 1 of the present invention.
Figure 12:
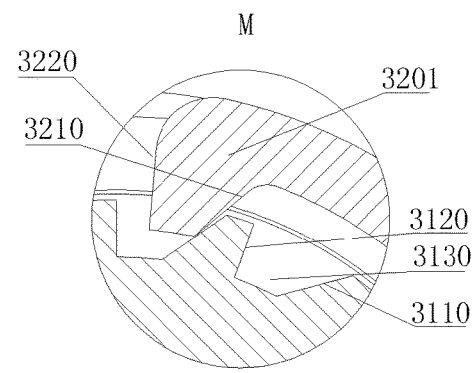
FIG. 12 is a partial enlarged view at M of FIG. 11.

2. As shown in FIGS. 11 and 12, the second implementation of the appropriate-rotation control mechanism 3000 is as follows.

The second implementation has a structure similar to that of the first implementation, in which each of the elastic snap heads 3201 adopts an elastic pawl, but the positions of the elastic snap head 3201 and the snap groove 3130 are exchanged. That is, the appropriate-stopper 3200 is multiple snap grooves 3130 disposed on the outer wall of the driving connector 3400, and at least one elastic snap head 3201 is disposed on the inner wall of the handwheel 3100; and the number of the elastic snap head 3201 is set according to an actual requirement, and may be multiple or one. The specific structures of the elastic snap head 3201 and the snap groove 3130 are the same as those of the first implementation, and thus will not be repeated anymore here.

Figure 13:
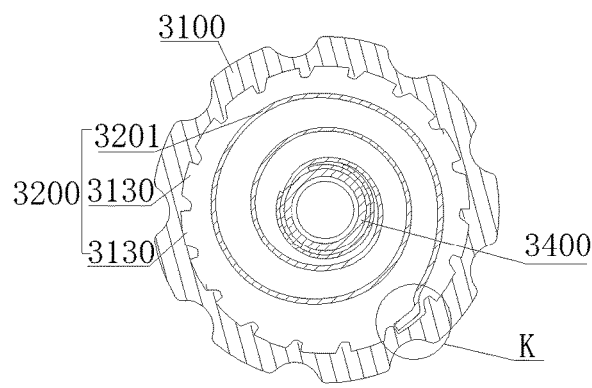
FIG. 13 is a schematic structural view of a third implementation of the appropriate-rotation control mechanism in Embodiment 1 of the present invention.
Figure 14:
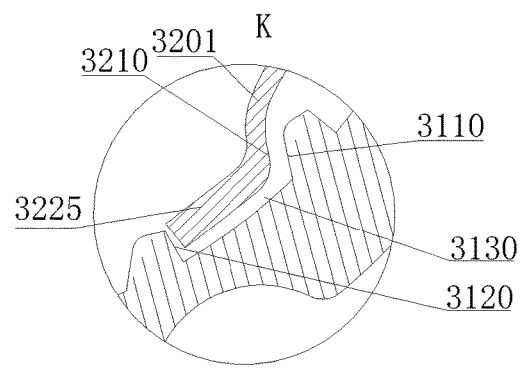
FIG. 14 is a partial enlarged view at K of FIG. 13.

3. As shown in FIGS. 13 and 14, the third implementation of the appropriate-rotation control mechanism 3000 is as follows.

The third implementation is replacing the elastic snap head 3201 from the elastic pawl to a helical spring strip on the basis of the first implementation and the second implementation. The helical spring strip is wound around the driving connector 3400 for several rounds. The helical spring strip generates an elastic force for stretching, and a free end 3225 of the helical spring strip is pressed into the snap groove 3130. The end portion of the free end 3225 of the helical spring strip may also be provided with a second sliding surface 3201, or alternatively may be not provided with a sliding surface. The helical direction of the helical spring strip is the same as the rotation direction of the handwheel 3100, both being counterclockwise. During assembly, the handwheel 3100 is rotated such that the helical spring strip contacts the first sliding surface 3110 of the snap groove 3130 at the overlapped portion of the helical spring strip and the first sliding surface 3110, and at this time the thread tightening force of the position-limiting locking connector 1100 is smaller than the elastic force by which the helical spring strip expands outwardly, and drives the rotation of the position-limiting locking connector 1100, such that the threads are tightened normally; when the end surface 1410 of the loading tube 1000 contacts the stage 2111 of the delivery sheath 2000, the thread tightening is prevented, and the position-limiting locking connector 1100 cannot rotate any more, and at this time the handwheel 3100 is rotated continually and thus the tightening resistance is increased, and when the resistance is greater than the force by which the helical spring strip is elastically deformed, the helical spring strip is elastically deformed, and the first sliding surface 3110 slides out from the free end of the helical spring strip; such that it achieves that the handwheel 3100 is rotated while the position-limiting locking connector 1100 is not rotated, thereby avoiding the damage to the end surface 1410 due to extrusion deformation caused by the excessive tightening of the threads. At the moment when the first sliding surface 3110 slides out, the elastically-deformed helical spring strip is recovered and makes a collision with the handwheel 3100 to make a sound, so as to prompt an operator that the assembly has been in place, and it does not need to continue to rotate the handwheel 3100. When the handwheel 3100 is rotated in an opposite direction, the first stopping surface 3120 of the snap groove 3130 contacts the free end of the helical spring strip, and the outer diameter of the helical spring strip is gradually increased under the action of the handwheel 3100, and when the outer diameter is increased to extrude the driving portion, the position-limiting locking connector 1100 can be driven to rotate in the opposite direction; and when the threads are rotated out, the rotating force of the threads is gradually reduced, such that the rotation of the handwheel 3100 can easily drive the rotation of the position-limiting locking connector 1100, thereby achieving the separation of the loading tube 1000 from the delivery sheath 2000.

Figure 15:
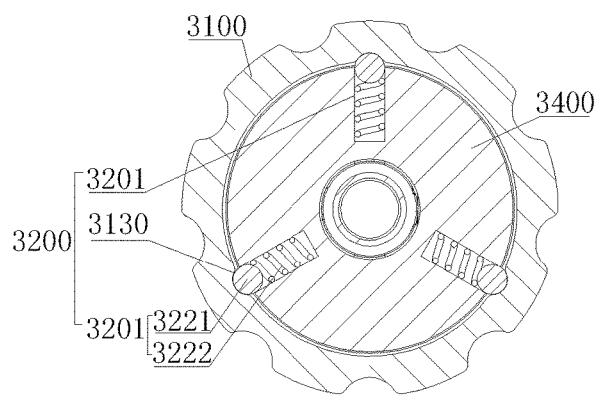
FIG. 15 is a schematic structural view of a fourth implementation of the appropriate-rotation control mechanism in Embodiment 1 of the present invention when it is locked.
Figure 16:
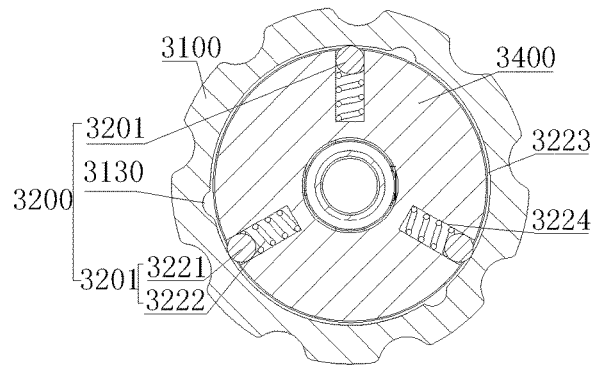
FIG. 16 is a schematic structural view of the fourth implementation of the appropriate-rotation control mechanism in Embodiment 1 of the present invention when it slides.

4. As shown in FIGS. 15 and 16, the fourth implementation of the appropriate-rotation control mechanism 3000 is as follows.

The fourth implementation is replacing the elastic snap head 3201 from the elastic pawl to an elastic member 3222 and a top-pressing member 3221 disposed on the front end of the elastic member 3222, on the basis of the first implementation and the second implementation. In this Embodiment, preferably the elastic member 3222 is a spring, and the top-pressing member 3221 is a steel bead. The snap groove 3130 is a semicircular groove with one side thereof being set as rounded, such that the radian of one side of the semicircular groove tends to be flat, and the steel beads slides out from the snap groove 3130 easily. Multiple snap grooves 3130 are disposed evenly along the circumference on the outer wall of the driving connector 3400 or the inner wall of the handwheel 3100, and three snap grooves 3130 are disposed in this Embodiment. In order to allow the steel beads to rotate circumferentially on the circumference, an annular raceway 3223 is disposed on the driving connector 3400 or the inner wall of the handwheel 3100, and the snap groove 3130 is disposed in the raceway 3223. In order to make the spring only extend radially, multiple blind holes 3224 are disposed on the driving connector 3400 and the inner walls of the handwheel 3100 along a radial direction, the spring is fixed in the blind hole 3224, and the spring can only extend or contract in the blind hole 3224.

Under a normal state, the top-pressing member 3221 is supported by the elastic member 3222, and is snapped in the snap groove 3130 (semicircular groove) of the handwheel 3100; when the loading tube 1000 is assembled with the delivery sheath 2000, the handwheel 3100 is rotated to drive the top-pressing member 3221, the elastic member 3222 and the position-limiting locking connector 1100 to rotate simultaneously, such that the threads are tightened normally; when the end surface 1410 of the loading tube 1000 contacts the stage 2111 of the delivery sheath 2000, the thread tightening is prevented and the position-limiting locking connector 1100 cannot be rotated any more. At this time, the handwheel 3100 is rotated continually, and the rotation resistance is increased. When the resistance is greater than the elastic force applied by the elastic member 3222 onto the top-pressing member 3221, the elastic member 3222 is compressed and thus the top-pressing member 3221 moves back to slide from the snap groove 3130 (semicircular groove) into the raceway 3223 disposed on the inner wall of the handwheel 3100, such that it achieves that the handwheel 3100 is rotated while the position-limiting locking connector 1100 is not rotated, thereby avoiding the damage to the end surface 1410 due to extrusion deformation caused by the excessive tightening of the threads. The handwheel 3100 is rotated continually, and the top-pressing member 3221 is snapped into the next snap groove 3130 under the elastic action of the elastic member 3222 and makes a sound, so as to prompt an operator that the assembly has been in place, and it does not need to continue to rotate the handwheel 3100. When the handwheel 3100 is rotated in an opposite direction, since the other surface of the snap groove 3130 is not rounded, the resistance applied on the top-pressing member 3221 is larger than the tightening force, and when the threads are rotated out, the rotating force of the threads is gradually reduced, such that the top-pressing member 3221 is always snapped in the snap groove 3130 under the action of the elastic member 3222 and drives the rotation of the position-limiting locking connector 1100, thereby achieving the separation of the loading tube 1000 from the delivery sheath 2000.

Figure 17:
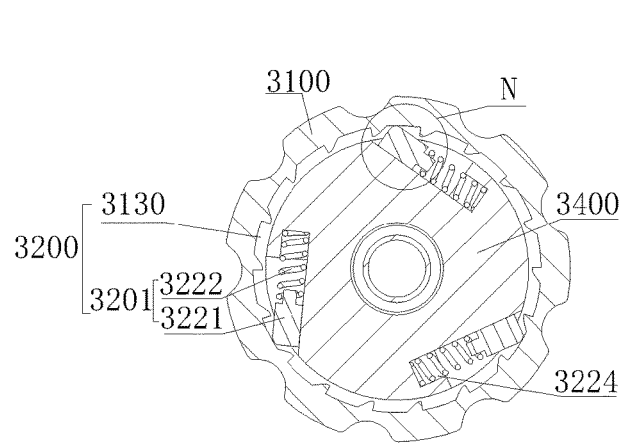
FIG. 17 is a schematic structural view of a fifth implementation of the appropriate-rotation control mechanism in Embodiment 1 of the present invention.
Figure 18:
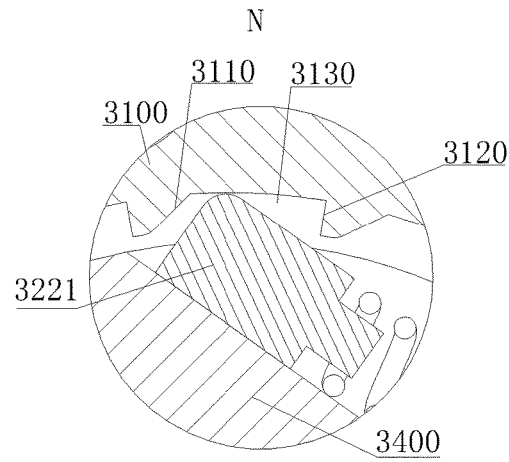
FIG. 18 is a partial enlarged view at N of FIG. 17.

5. As shown in FIGS. 17 and 18, the fifth implementation of the appropriate-rotation control mechanism 3000 is as follows.

The fifth implementation is replacing the top-pressing member 3221 from the steel bead to a movable pin on the basis of the fourth implementation. The snap groove 3130 adopts the structure of the snap groove in the first to third implementation, and the blind hole 3224 is changed from disposing in the radial direction to deflecting towards a counterclockwise direction or a clockwise direction, such that the external end of the movable pin shifts towards the counterclockwise direction or the clockwise direction, and is abutted against the first sliding surface 3110 of the snap groove 3130.

Under a normal state, the movable pin serving as the top-pressing member 3221 is supported by the elastic force of the elastic member 3222, and is snapped in the snap groove 3130; when the loading tube 1000 is assembled with the delivery sheath 2000, the handwheel 3100 is rotated, the first sliding surface 3110 of the snap groove 3130 contacts the movable pin serving as the top-pressing member 3221 to drive the motion of the elastic member 3222, and the position-limiting locking connector 1100 is also rotated simultaneously, such that the threads are tightened normally; when the end surface 1410 of the loading tube 1000 contacts the stage 2111 of the delivery sheath 2000, the thread tightening is prevented and the position-limiting locking connector 1100 cannot be rotated continually. At this time, the handwheel 3100 is rotated continually, and the rotation resistance is increased. When the rotation resistance is greater than the elastic force of the elastic member 3222, the elastic member 3222 is compressed and thus the movable pin serving as the top-pressing member 3221 moves back, and the first sliding surface 3110 slides over the movable pin serving as the top-pressing member 3221, such that it achieves that the handwheel 3100 is rotated while the position-limiting locking connector 1100 is not rotated, thereby avoiding the damage to the end surface 1410 due to extrusion deformation caused by the excessive tightening of the threads. At the moment when the first sliding surface 3110 slides out, the movable pin serving as the top-pressing member 3221 returns to its original position under the action of the elastic member 3222, and the movable pin serving as the top-pressing member 3221 makes a collision with the handwheel 3100 to make a sound, so as to prompt an operator that the assembly has been in place, and it does not need to continue to rotate the handwheel 3100. When the handwheel 3100 is rotated in an opposite direction, the first stopping surface 3120 of the snap groove 3130 contacts the movable pin serving as the top-pressing member 3221. At this time, the force applied by the first stopping surface 3120 on the movable pin serving as the top-pressing member 3221 is perpendicular to the elastic force of the elastic member 3222, such that the elastic member 3222 does not contract, and the movable pin serving as the top-pressing member 3221 does not move back. The position-limiting locking connector 1100 is driven to rotate in the opposite direction, thereby achieving the separation of the loading tube 1000 from the delivery sheath 2000.

Embodiment 2, the difference between the structure of this Embodiment and that of Embodiment 1 is that: in addition to the position-limiting locking connector 1100 and the appropriate-rotation control mechanism 3000 being respectively disposed on the loading tube 1000 of the loader or on the delivery sheath 2000, the position-limiting locking connector 1100 and the appropriate-rotation control mechanism 3000 are disposed separately, and the appropriate-rotation control mechanism 3000 and the position-limiting locking connector 1100 are engaged with each other only after the loading tube 1000 or the delivery sheath 2000 is engaged, such that the appropriate-rotation control mechanism 3000 drives the position-limiting locking connector 1100 to rotate.

Figure 19:
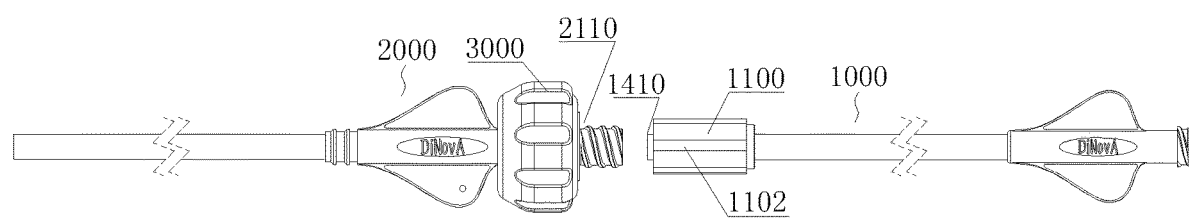
FIG. 19 is a schematic structural view of Example 2 of the present invention.
Figure 20:
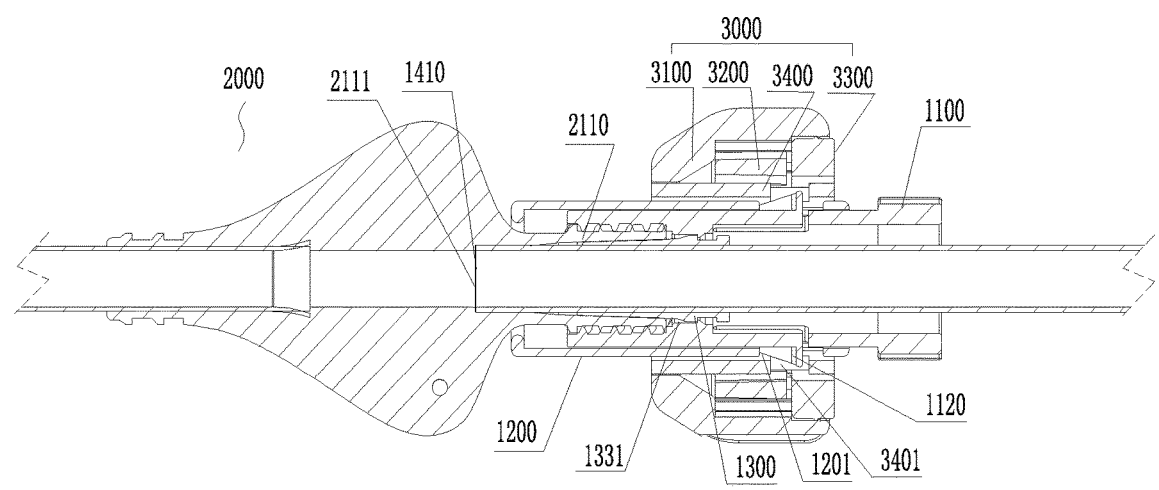
FIG. 20 is a schematic structural view of the appropriate-rotation control mechanism assembled to the loading tube in Embodiment 2 of the present invention.

As shown in FIGS. 19 and 20, the position-limiting locking connector 1100 is disposed on the loading tube 1000 of the loader, and the appropriate-rotation control mechanism 3000 is disposed on the delivery sheath 2000. The position-limiting locking connector 1100 may also be disposed on the proximal connection portion of the delivery sheath 2000, and the appropriate-rotation control mechanism 3000 may also be disposed on the distal connection portion of the loading tube 1000 of the loader.

The fixation manners of the position-limiting locking connector 1100 and the appropriate-rotation control mechanism 3000 on the distal connection portion of the loading tube 1000 and the proximal connection portion of the delivery sheath 2000, as well as the structures of themselves are the same as those of the Embodiment 1, and thus will not be repeated anymore here.

As shown in FIGS. 19 and 20, there are many manners for engaging the appropriate-rotation control mechanism 3000 and the position-limiting locking connector 1100, and generally the engagement manner is that an engagement block and an engagement groove, which are disposed axially, engage with each other. The engagement block and the engagement groove may be disposed on the wall surfaces of the appropriate-rotation control mechanism 3000 and the position-limiting locking connector 1100, and may also be disposed on the end portions at which the appropriate-rotation control mechanism 3000 and the position-limiting locking connector 1100 are connected. As shown in FIG. 19, an engagement groove 1102 is disposed on the surface of the outer wall of the position-limiting locking connector 1100 along an axial direction, and a protrusion or flange (not shown) is disposed on the surface of the inner wall of the corresponding appropriate-rotation control mechanism 3000, and when the protrusion or flange is engaged into the engagement groove 1102, the appropriate-rotation control mechanism 3000 drives the position-limiting locking connector 1100 to rotate. The protrusion or flange is disposed on the surface of the inner wall of the appropriate-rotation control mechanism 3000, and particularly on the surface of the inner wall of the driving connector 3400; and a protrusion or flange may also be disposed on the outer wall of the position-limiting locking connector 1100 along the axial direction, an engagement groove is disposed axially on the corresponding appropriate-rotation control mechanism 3000, and the protrusion or flange and the engagement groove engage with each other.

The other structures of this Embodiment are the same as those of Embodiment 1, and thus will not be repeated anymore here.

Figure 21:
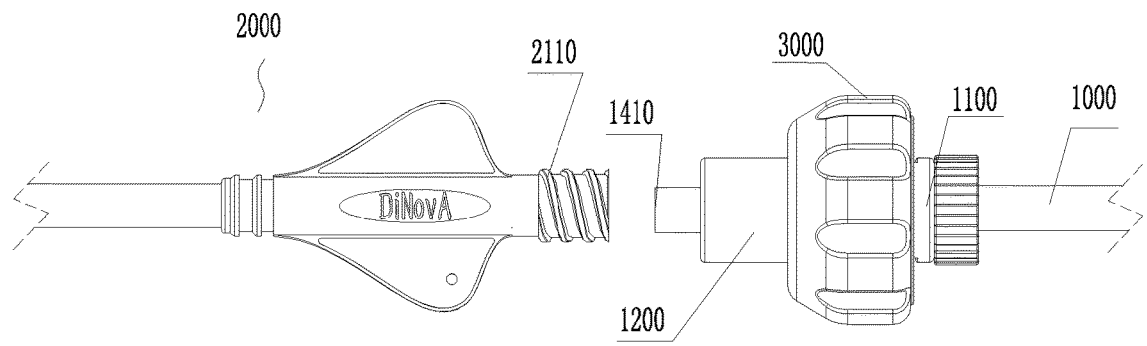
FIG. 21 is a schematic structural view of Embodiment 3 of the present invention.
Figure 22:
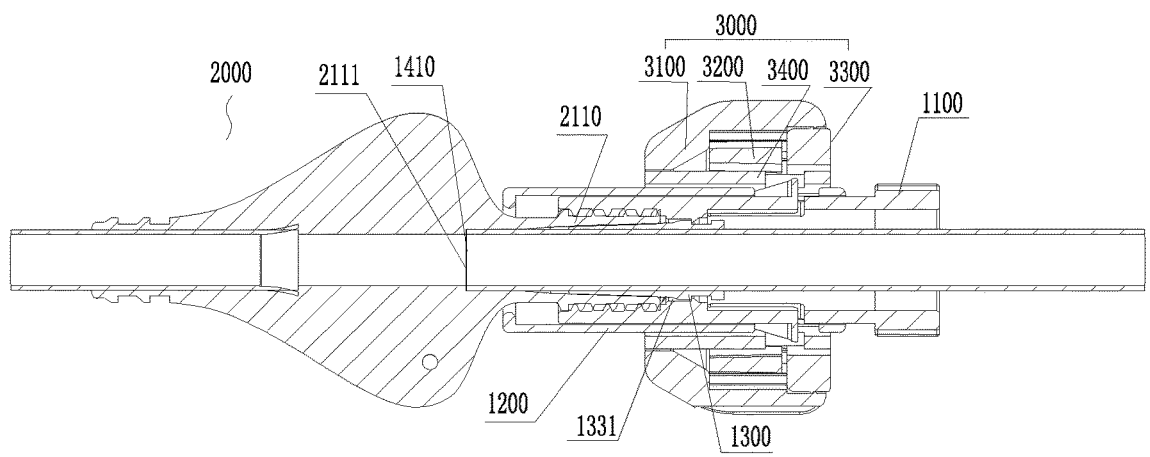
FIG. 22 is a cross-sectional view of Embodiment 3 of the present invention.

Embodiment 3, as shown in FIGS. 21 and 22, this Embodiment is on the basis of Embodiment 1, in which the position-limiting locking connector 1100 and the appropriate-rotation control mechanism 3000 are connected through a connecting sleeve 1200, the connecting sleeve 1200 is sleeved outside the position-limiting locking connector 1100, and the appropriate-rotation control mechanism 3000 is sleeved outside the connecting sleeve 1200. That is, the position-limiting locking connector 1100 and the connecting sleeve 1200, as well as the connecting sleeve 1200 and the appropriate-rotation control mechanism 3000, are each detachably connected to each other. The structures of the position-limiting locking connector 1100 and the appropriate-rotation control mechanism 3000 are the same as those of Embodiment 1, and thus will not be repeated anymore here.

The connecting sleeve 1200 is a tubular structure having an inner diameter which is slightly larger than the outer diameter of the position-limiting locking connector 1100, and a sliding gap is retained between the connecting sleeve 1200 and the position-limiting locking connector 1100.

Some elastic positioning member and some snapping position are respectively disposed among the position-limiting locking connector 1100, the connecting sleeve 1200, and the appropriate-rotation control mechanism 3000, to achieve the detachable connection among the three ones.

The detachable connection implementations are as follows: one implementation is the one in which the position-limiting locking connector 1100, the connecting sleeve 1200, and the driving connector 3400 of the appropriate-rotation control mechanism 3000 are each independently provided with at least one of a snapping position and an elastic positioning member, and the adjacent components are fixed detachably through snap connection; and another implementation is the one as shown in FIG. 20, in which an elastic positioning member 1120 is disposed on the outer wall of the position-limiting locking connector 1100, the connecting sleeve 1200 is provided with a snapping position 1201 correspondingly, the driving connector 3400 of the appropriate-rotation control mechanism 3000 is provided with a snapping position 3401, the elastic positioning member 1120 is simultaneously snapped into the snapping positions 1201 and the snapping position 3401, to connect the three ones together.

The other structures are the same as those of Embodiment 1, and thus will not be repeated anymore here.

Figure 23:
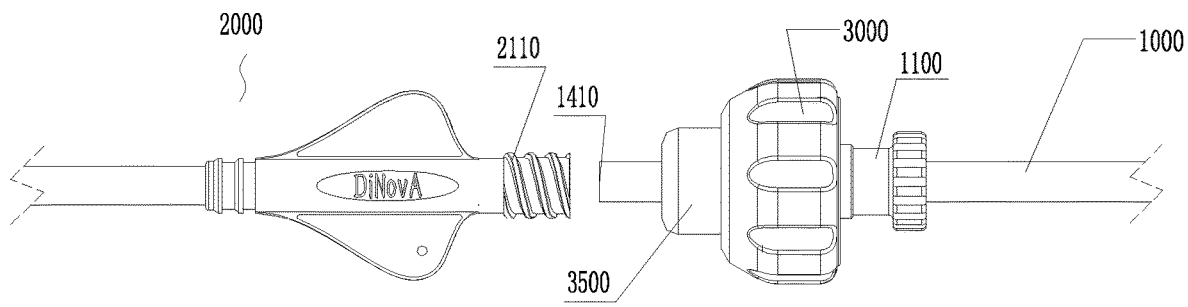
FIG. 23 is a schematic structural view of Embodiment 4 of the present invention.
Figure 24:
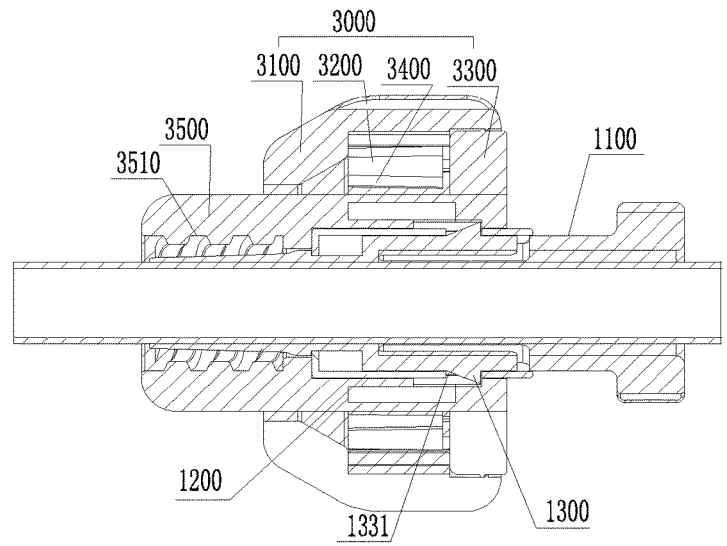
FIG. 24 is a cross-sectional view of Embodiment 4 of the present invention.

Embodiment 4, as shown in FIGS. 23 and 24, the difference between this Embodiment and the aforementioned Embodiment is that: the position-limiting locking connector 1100 and the appropriate-rotation control mechanism 3000 are integral structure, that is the driving connector 3400 is provided with a connection end 3500 which extends outwardly along the axial direction, the connection end 3500 is opened in the axial direction and is provided with an internal thread 3510 on the inner wall thereof, the position-limiting locking connector 1100 and the appropriate-rotation control mechanism 3000 are disposed at an distal end of the loading tube 1000, and the internal thread 3510 of the connection end 3500 engages with the external thread 2110 located at the proximal end of the delivery sheath 2000, such that the proximal end of the delivery sheath 2000 and the distal end of the loading tube 1000 are connected together fixedly.

Alternatively, the appropriate-rotation control mechanism 3000 is provided with a connection head therein, the connection head is fixedly connected to or detachably fixed to the appropriate-rotation control mechanism 3000, the connection head is opened at one end thereof in the axial direction and is provided with an internal thread on an inner wall thereof, and the internal thread of the connection head is threadingly connected to an external thread at an proximal end of the delivery sheath 2000 or an external thread at a distal end of the loading tube 1000, to fixedly connect the proximal end of the delivery sheath 2000 and the distal end of the loading tube 1000 together.

The position-limiting locking connector 1100, the connecting sleeve 1200, and the appropriate-rotation control mechanism 3000 themselves have the same structures as those of Embodiment 1-3, and thus will not be repeated anymore here.

Figure 25:
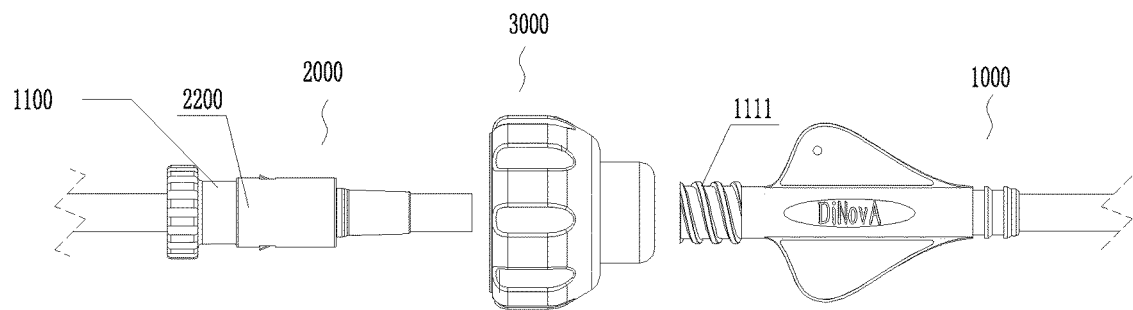
FIG. 25 is a schematic structural view of Embodiment 5 of the present invention.
Figure 26:
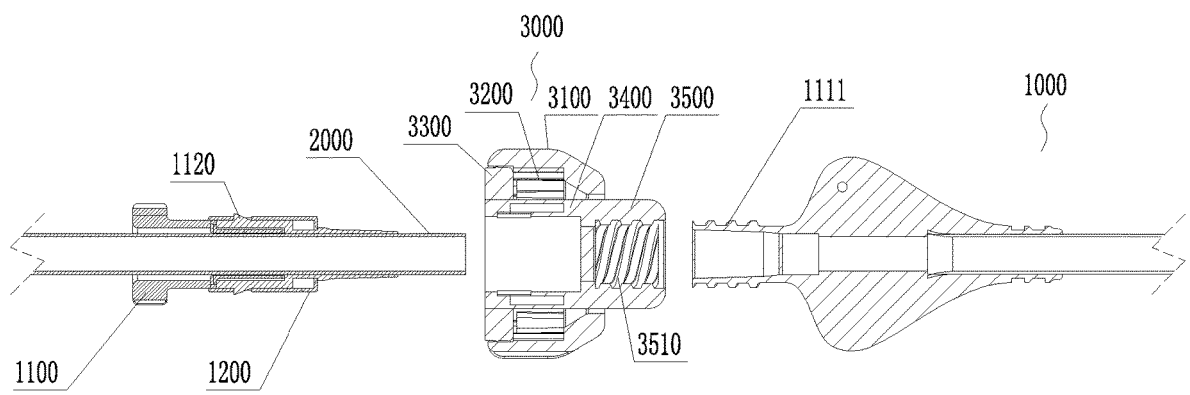
FIG. 26 is a cross-sectional view of Embodiment 5 of the present invention.

Embodiment 5, as shown in FIGS. 25 and 26, this Embodiment is an improvement on the basis of Embodiment 4, and the difference between this Embodiment and the aforementioned Embodiment 4 is that: the position-limiting locking connector 1100 and the appropriate-rotation control mechanism 3000 are integral structure, and the integral structure is disposed on the proximal end of the delivery sheath 2000, and the internal thread 3510 of the connection end 3500 engages with the external thread 1111 of the loading tube 1000, such that the proximal end of the delivery sheath 2000 and the distal end of the loading tube 1000 are connected together fixedly. The position-limiting locking connector 1100, the connecting sleeve 1200, and the appropriate-rotation control mechanism 3000 themselves have the same structures as those of Embodiments 1-4, and thus will not be repeated anymore here.

Figure 27:
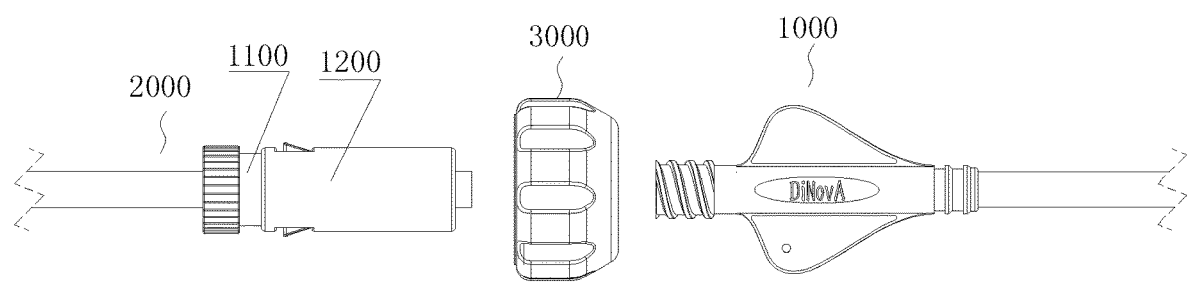
FIG. 27 is a schematic structural view of Embodiment 6 of the present invention.
Figure 28:
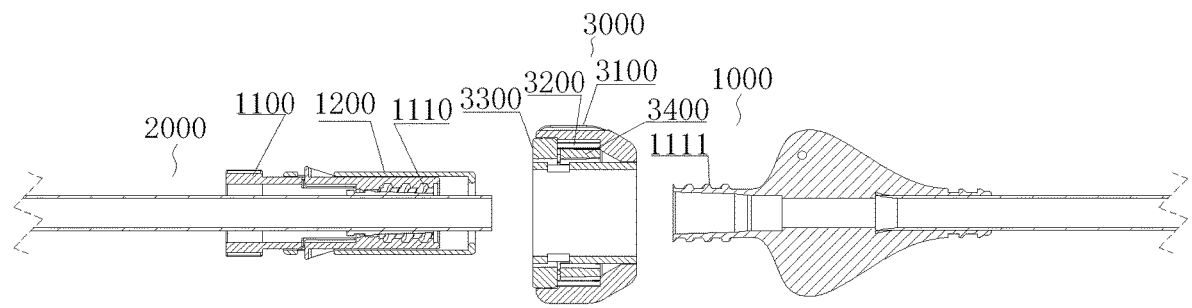
FIG. 28 is a cross-sectional view of Embodiment 6 of the present invention.

Embodiment 6, as shown in FIGS. 27 and 28, this Embodiment is based on Embodiment 1, in which the connecting sleeve 1200 is added between the position-limiting locking connector 1100 and the appropriate-rotation control mechanism 20003000. The three ones are all disposed on the proximal outer wall of the delivery sheath 2000. The difference between the Embodiment 6 and the Embodiment 5 is that: the position-limiting locking connector 1100 is provided with an internal thread 1110 which engages with the external thread 1111 located at the distal end of the loading tube 1000, and the remaining structures are the same as those of Embodiment 5, and thus will not be repeated anymore here.

What is claimed is:

1. An interventional medical device delivery system, comprising a loader provided with a loading tube, a delivery sheath, a dilator, a pushing component and a hemostasis valve, wherein:
   the loading tube or the delivery sheath is provided with a position-limiting locking connector thereon;
   an appropriate-rotation control mechanism for controlling a tightening degree between a distal end of the loading tube and a proximal end of the delivery sheath is disposed outside the loading tube or the delivery sheath;
   the proximal end of the delivery sheath and the distal end of the loading tube engage with each other in a sealed manner, and are threadingly fixed to each other by means of the position-limiting locking connector; and the appropriate-rotation control mechanism rotates in one direction to appropriately tighten a thread-connection, and rotates in the opposite direction to release the thread-connection;
   wherein the position-limiting locking connector and the appropriate-rotation control mechanism are simultaneously sleeved outside the loading tube or the delivery sheath; the appropriate-rotation control mechanism and the position-limiting locking connector are engaged, fixedly connected, or detachably fixed with each other; the position-limiting locking connector is provided with an internal thread, the delivery sheath or loading tube is provided with an external thread correspondingly, and the internal thread and the external thread are threadingly connected to connect the loading tube and the delivery sheath together;
   wherein the appropriate-rotation control mechanism is detachably fixed with the position-limiting locking connector through an elastic positioning member and a snapping position; the position-limiting locking connector is provided with the elastic positioning member on the outer wall thereof, the appropriate-rotation control mechanism is provided with the snapping position thereon correspondingly, the elastic positioning member is elastically snapped into the snapping position to detachably fix the appropriate-rotation control mechanism and the position-limiting locking connector, and under an external force, the elastic positioning member elastically contracts and thus is detached from the snapping position to release the fixation between the appropriate-rotation control mechanism and the position-limiting locking connector; or
   alternatively, the appropriate-rotation control mechanism is provided with the elastic positioning member, and the position-limiting locking connector is provided with a snapping position thereon correspondingly, the elastic positioning member is elastically snapped into the snapping position to detachably fix the appropriate-rotation control mechanism and the position-limiting locking connector, and under the external force, the elastic positioning member elastically contracts and thus is detached from the snapping position to release the fixation between the appropriate-rotation control mechanism and the position-limiting locking connector.

2. The interventional medical device delivery system of claim 1, wherein the elastic positioning member is an elastic member which is fixed on the position-limiting locking connector and gradually stretches outwardly from the wall of the position-limiting locking connector, and after the elastic positioning member is elastically snapped into the snapping position, the appropriate-rotation control mechanism is position-limiting fixed and only rotates relative to the position-limiting locking connector; or
   alternatively, the elastic positioning member is an elastic member which is fixed in the appropriate-rotation control mechanism and gradually stretches from the appropriate-rotation control mechanism to a center, and after the elastic positioning member is snapped into the snapping position, the appropriate-rotation control mechanism is position-limiting fixed and only rotates relative to the position-limiting locking connector.

3. An interventional medical device delivery system, comprising a loader provided with a loading tube, a delivery sheath, a dilator, a pushing component and a hemostasis valve, wherein:
   the loading tube or the delivery sheath is provided with a position-limiting locking connector thereon;
   an appropriate-rotation control mechanism for controlling a tightening degree between a distal end of the loading tube and a proximal end of the delivery sheath is disposed outside the loading tube or the delivery sheath;
   the proximal end of the delivery sheath and the distal end of the loading tube engage with each other in a sealed manner, and are threadingly fixed to each other by means of the position-limiting locking connector; and the appropriate-rotation control mechanism rotates in one direction to appropriately tighten a thread-connection, and rotates in the opposite direction to release the thread-connection;
   wherein the appropriate-rotation control mechanism and the position-limiting locking connector are respectively disposed outside the loading tube or the delivery sheath, and after the loading tube or the delivery sheath is engaged, the appropriate-rotation control mechanism and the position-limiting locking connector are engaged with each other, such that the appropriate-rotation control mechanism drives the position-limiting locking connector to rotate.

4. An interventional medical device delivery system, comprising a loader provided with a loading tube, a delivery sheath, a dilator, a pushing component and a hemostasis valve, wherein:
the loading tube or the delivery sheath is provided with a position-limiting locking connector thereon;
an appropriate-rotation control mechanism for controlling a tightening degree between a distal end of the loading tube and a proximal end of the delivery sheath is disposed outside the loading tube or the delivery sheath;
the proximal end of the delivery sheath and the distal end of the loading tube engage with each other in a sealed manner, and are threadingly fixed to each other by means of the position-limiting locking connector; and the appropriate-rotation control mechanism rotates in one direction to appropriately tighten a thread-connection, and rotates in the opposite direction to release the thread-connection;
wherein the position-limiting locking connector and the appropriate-rotation control mechanism are simultaneously sleeved outside the loading tube or the delivery sheath; the appropriate-rotation control mechanism and the position-limiting locking connector are engaged, fixedly connected, or detachably fixed with each other; the position-limiting locking connector is provided with an internal thread, the delivery sheath or loading tube is provided with an external thread correspondingly, and the internal thread and the external thread are threadingly connected to connect the loading tube and the delivery sheath together;
wherein the position-limiting locking connector and the appropriate-rotation control mechanism are connected through a connecting sleeve; and the position-limiting locking connector and the connecting sleeve, as well as the connecting sleeve and the appropriate-rotation control mechanism, are each detachably connected.

5. The interventional medical device delivery system of claim 4, wherein the position-limiting locking connector, the connecting sleeve and the appropriate-rotation control mechanism are each provided with an elastic positioning member and/or a snapping position thereon; and the position-limiting locking connector and the connecting sleeve, as well as the connecting sleeve and the appropriate-rotation control mechanism, are detachably fixed together through the elastic positioning member being elastically snapped into the snapping position.

6. The interventional medical device delivery system of claim 5, wherein the appropriate-rotation control mechanism comprises a handwheel, the handwheel is therein provided with a driving connector that is detachably fixed to the connecting sleeve or the position-limiting locking connector, and an appropriate-stopper is arranged between the handwheel and the driving connector; the handwheel drives the driving connector to rotate with a driving force that is less than a force which forces the appropriate-stopper to be deformed to slide out, and the handwheel drives the driving connector to rotate towards a direction by means of the appropriate-stopper; when the driving force by which the handwheel drives the driving connector to rotate during tightening causes that the appropriate-stopper is deformed to slide out, the handwheel independently rotates relative to the driving connector.

7. The interventional medical device delivery system of claim 6, wherein the appropriate-stopper is at least one elastic snap head disposed on an inner wall of the handwheel, and the corresponding driving connector is provided with multiple snap grooves on an outer wall thereof; or alternatively the appropriate-stopper is at least one elastic snap head disposed on an outer wall of the driving connector, and the handwheel is correspondingly provided with multiple snap grooves on an inner wall thereof;
each snap groove is provided with a first sliding surface on a side wall thereof; after the elastic snap head is snapped into the snap groove, an end portion of the elastic snap head is lap-jointed with the first sliding surface, and the rotation of the handwheel drives the driving connector to rotate; and
when the driving connector is stopped as subjected to a rotation resistance, the rotation of the handwheel forces the elastic snap head to deform elastically and thus slides out from the snap groove through the first sliding surface, and the handwheel spins relative to the driving connector; a side surface of the snap groove that is opposite to the first sliding surface is a first stopping surface, and an end portion of the elastic snap head is lap-jointed with the first stopping surface such that the handwheel rotates in an opposite direction to drive the driving connector to rotate.

8. The interventional medical device delivery system of claim 6, wherein the driving connector has a connection end that extends outwardly along an axial direction, the connection end is opened in the axial direction and is provided with an internal thread on an inner wall thereof, and the internal thread of the connection end is threadingly connected to an external thread at a proximal end of the delivery sheath or an external thread at a distal end of the loading tube so as to fixedly connect the proximal end of the delivery sheath and the distal end of the loading tube together; or
alternatively the appropriate-rotation control mechanism is provided with a connection head therein, the connection head is fixedly connected to or detachably fixed to the appropriate-rotation control mechanism, the connection head is opened at one end thereof in the axial direction and is provided with an internal thread on an inner wall thereof, and the internal thread of the connection head is threadingly connected to an external thread at an proximal end of the delivery sheath or an external thread at a distal end of the loading tube to fixedly connect the proximal end of the delivery sheath and the distal end of the loading tube together.

9. The interventional medical device delivery system of claim 7, wherein the elastic snap head is a helical spring strip, or an elastic pawl that is bendable under a force; or alternatively the elastic snap head comprises an elastic member, and a top-pressing member disposed at a front end of the elastic member.

10. The interventional medical device delivery system of claim 4, wherein the appropriate-rotation control mechanism comprises a handwheel, the handwheel is therein provided with a driving connector that is detachably fixed to the connecting sleeve or the position-limiting locking connector, and an appropriate-stopper is arranged between the handwheel and the driving connector; the handwheel drives the driving connector to rotate with a driving force that is less than a force which forces the appropriate-stopper to be deformed to slide out, and the handwheel drives the driving connector to rotate towards a direction by means of the appropriate-stopper; when the driving force by which the handwheel drives the driving connector to rotate during tightening causes that the appropriate-stopper is deformed to slide out, the handwheel independently rotates relative to the driving connector.

\* \* \* \* \*